United States Patent
Lappe et al.

(12)

(10) Patent No.: US 6,623,979 B2
(45) Date of Patent: Sep. 23, 2003

(54) SYSTEM FOR COLLECTING AND LOCALLY ANALYZING A FLUID SPECIMEN

(75) Inventors: Murray Lappe, Beverly Hills, CA (US); John W. Goodin, Coto de Caza, CA (US); Keith Patten, Los Angeles, CA (US); Bill Whitford, Woodland Hills, CA (US)

(73) Assignee: Escreen, Overland Park, KS (US)

( * ) Notice: Subject to any disclaimer, the term of this patent is extended or adjusted under 35 U.S.C. 154(b) by 0 days.

(21) Appl. No.: 09/971,855

(22) Filed: Oct. 4, 2001

(65) Prior Publication Data

US 2002/0009390 A1 Jan. 24, 2002

Related U.S. Application Data

(60) Division of application No. 09/245,175, filed on Feb. 5, 1999, now Pat. No. 6,342,183, which is a continuation-in-part of application No. 08/832,957, filed on Apr. 4, 1997, now Pat. No. 5,929,422, and a continuation-in-part of application No. 08/801,041, filed on Feb. 14, 1997, now Pat. No. 5,916,815, and a continuation-in-part of application No. 09/018,487, filed on Feb. 4, 1998, now Pat. No. 6,036,092, and a continuation-in-part of application No. 09/025,559, filed on Feb. 18, 1998, now Pat. No. 5,902,982.

(51) Int. Cl.[7] .................. G01N 21/03; G01N 33/493; G01N 33/48

(52) U.S. Cl. .................. 436/165; 436/166; 436/169; 436/807; 436/808; 422/50; 422/68.1

(58) Field of Search .................. 436/44, 165, 166, 436/169, 807, 808; 422/68.1, 50

(56) References Cited

U.S. PATENT DOCUMENTS 5,620,898 A * 4/1997 Yaremko et al. .............. 422/63
5,849,505 A * 12/1998 Guirguis ..................... 422/101

* cited by examiner

*Primary Examiner*—Jill Warden
*Assistant Examiner*—LaToya Cross
(74) *Attorney, Agent, or Firm*—Hovey Williams LLP (57) ABSTRACT

A method and apparatus for collecting a fluid specimen, locally analyzing the specimen to qualitatively detect specified chemical components at concentrations above threshold levels, and providing machine readable test results for facilitating data collection and reporting. The apparatus includes an assaying device comprised of a cup for collecting a fluid specimen and a cap carrying at least one test strip for visually reacting to one or more specified chemical components in the specimen. The cap also carries an aliquot delivery mechanism for forcing an aliquot of the fluid specimen onto the test strip. The assaying device is preferably configured to interact with a reader device capable of reading the reaction of the test strip to produce a data output.

3 Claims, 9 Drawing Sheets

SYSTEM FOR COLLECTING AND LOCALLY ANALYZING A FLUID SPECIMEN

RELATED APPLICATIONS

This application is a divisional of Ser. No. 09/245,175, filed Feb. 5, 1999 now U.S. Pat. No. 6,342,183, which is a Continuation-In-Part of U.S. application Ser. No. 08/832,957 filed Apr. 4, 1997 by Murray Lappe, now U.S. Pat. No. 5,929,422. U.S. applications Ser. No. 08/801,041 filed Feb. 14, 1997, now U.S. Pat. No. 5,916,815; 09/018,487 filed Feb. 4, 1998, now U.S. Pat. No. 6,036,092; and 09/025,559 filed Feb. 18, 1998, now U.S. Pat. No. 5,902,982 are also related. The disclosures of the aforementioned applications are, by reference, incorporated herein.

BACKGROUND OF THE INVENTION

This invention relates to a system and components thereof for collecting and locally analyzing fluid specimens, e.g., body fluids such as urine.

Devices for collecting and locally analyzing body fluids have been described in the patent literature, as exemplified by U.S. Pat. No. 5,403,551. Such devices may be used, for example, by employers to screen employee applicants for illegal drug use. As noted in U.S. Pat. No. 5,403,551, it is desirable for drug screening tests to be locally performed, i.e., at the collection site, for the purpose of quickly determining on a qualitative basis whether specific drugs are present in a fluid specimen, typically, urine. If the results of the screening test are positive, a more complete quantitative analysis is subsequently performed, typically, at a remote laboratory site. Inasmuch as it is extremely important to positively correlate the specimen with the person being tested, U.S. Pat. No. 5,403,551, describes an assaying device that minimizes possible contamination of the specimen after the specimen is first collected. More particularly, U.S. Pat. No. 5,403,551 describes a device which functions to both collect and locally analyze a specimen. The device comprises a container for collecting and storing the specimen, a cap for sealing the container, and an assay means attached to the container for qualitatively analyzing a portion of the specimen. The assay means is described as using a plurality of latex/antibody chromatograph strips. Since the specimen does not have to be transferred out of the container for qualitative testing, if the initial test produces a positive result, the entire device containing the specimen can then be shipped to a laboratory for quantitative analysis.

The aforementioned Lappe applications variously describe machine readable assaying systems employing test or assaying cards bearing test or analysis strips thereon. The strips are configured such that when wetted by a fluid, they will react to visually indicate the presence of certain detectable substances in the fluid. The format of the visual indications can be of many different types capable of being machine read by a suitable reading apparatus.

SUMMARY OF THE INVENTION

The present invention is directed to a method and apparatus for collecting a fluid specimen and locally analyzing the specimen to qualitatively detect specified chemical components therein. More particularly, the invention is directed to such an apparatus which provides machine readable test results for facilitating the data collection and reporting of the results.

Apparatus in accordance with the invention includes an assaying device comprised of a cup for collecting a fluid specimen and a cap carrying at least one test strip for visually reacting to one or more specified chemical components in the specimen. The assaying device is preferably configured to interact with a reader device capable of reading the reaction of the test strip to produce an electronic data output.

One example of a test strip suitable for use with embodiments of the invention comprises membrane strips precoated with drug protein conjugates deposited on defined bands of the strip. Such strips are commercially available as the InstaCheck Multi-Drug Screen Panel manufactured by Forefront Diagnostics. Inc. of Laguna Hills, Calif.

In accordance with a preferred embodiment of the present invention, the assaying device carries one or more test strips which collectively test for multiple characteristics of the fluid specimen including the presence of specific chemical components at concentrations above threshold levels, the authenticity of the specimen (as, for example. whether it is freshly voided urine), and whether or not the specimen has been adulterated.

A preferred assaying device in accordance with the invention includes an open cup defining an interior volume for accommodating a fluid specimen and an attachable cap configured for mounting on the cup to seal the interior volume. The cap carries at least one test strip and an aliquot delivery mechanism actuatable to wet the test strip with an aliquot derived from the fluid specimen. In a preferred embodiment of the invention, the aliquot delivery mechanism comprises a pump in the form of a plunger for forcing an aliquot of the fluid specimen onto the test strip. The plunger can be actuated either manually or automatically, e.g., by a piston controlled by a compatible reader device.

In accordance with the preferred embodiment, the aliquot delivery mechanism includes first and second concentric tubular walls descending from the cap into the cup. A passageway is defined between the tubular walls having an inlet at its lower end for contacting the specimen in the cup and an outlet at its upper end for delivering an aliquot onto the test strip.

In accordance with a significant feature of the preferred embodiment, the descending tubular walls and interior cup floor are cooperatively configured to isolate a portion of the specimen when the cap is installed onto the cup. The plunger acts on this isolated portion to force a small part thereof, i.e., an aliquot, through the passageway onto the test strip.

Tests strips used in preferred embodiments of the invention provide a visual reaction to chemical components having a concentration in the aliquot greater than a threshold concentration. Preferably, each test strip functions so that a negative test result for one or more components causes a multiple number of visually discernable discrete bands to appear on the strip. The presence of a single component in excess of a threshold suppresses the development of at least one of the bands. Therefore, the absence of a visually discernable band indicates a positive test result for a particular chemical component associated with that band.

The cap is preferably configured with one or more compartments, each for accommodating a different test strip. The passageway, which may comprise multiple branches, extends to the compartment for delivering an aliquot thereto. The cap preferably also defines one or more catch basins to catch any excess fluid delivered by the aliquot delivery mechanism to the test strip.

The cap is preferably also configured to define a transparent area or window located relative to the test strip compartment to enable the strip visual reaction to be read by a machine, e.g., a digital camera and image processor, and/or a human.

In accordance with a preferred embodiment, the cap and cup are provided with cooperating coupling means (e.g., mating threads or a bayonet mount) configured to seal the cup interior volume when key exterior portions of the cap and cup are physically aligned. More particularly, when the cap is fully installed on the cup, a key external portion of the cap, e.g., a flat slotted area, aligns relative to a key external portion of the cup. When these key external portions align, the aforementioned interior tubular walls form an interior chamber for isolating the aforementioned portion of the specimen.

The exterior of the cap and cup preferably have an irregular periphery to facilitate easy manual handling. The periphery is preferably also shaped to assure its particular orientation in a receptacle of a compatible reader device. When inserted in the receptacle. the cap is properly positioned to enable the test strip in the cap to be read by an imager, e.g. a digital camera, housed in the reader device.

A preferred reader device in accordance with the invention includes a microprocessor based controller for actuating the aliquot delivery mechanism of an assaying device placed in the reader device receptacle. More particularly, the reader device preferably includes an actuatable piston for pressing the delivery mechanism plunger to deliver an aliquot to the test strip. Preferably, the piston remains engaged with the assaying device for the duration of the test (typically, up to eight minutes) to prevent a person from substituting specimens during the course of a test.

The reader device preferably includes a camera and image processor controlled by the controller for viewing the test strip of an assaying device to produce a positive or negative test result for the specimen contained therein. The test result data, along with identification data read from a label carried by the assaying device, can then be stored or communicated, e.g., via a modem.

Embodiments of the present invention are used primarily to perform local on-site screening while preserving an uncontaminated specimen for further analysis if necessary. That is, in typical use, embodiments of the present invention function to perform a qualitative analysis on an aliquot of the specimen to screen for negative results. If a negative result is not achieved, then the sealed assaying device containing the remaining uncontaminated specimen is typically shipped to a remote site for further analysis.

DETAILED DESCRIPTION

FIGS. 1–3, 9A, 9B depict the external configuration of a preferred assaying device 20 in accordance with the present invention. The assaying device 20 includes a housing 22 comprised of a cup 24 and a detachable cap 26. The cup 24 defines an interior volume for collecting a fluid specimen, e.g., a body fluid such as urine. After the fluid specimen has been deposited into the cup 24, the cap 26 is mounted thereon to seal the interior volume and prevent the fluid specimen from leaking. In a preferred utilization, each physical assaying device 20 will be used only once, i.e., to collect a single specimen. Accordingly, the assaying device components are all preferably fabricated via relatively low cost plastic molding processes.

Figure 1:
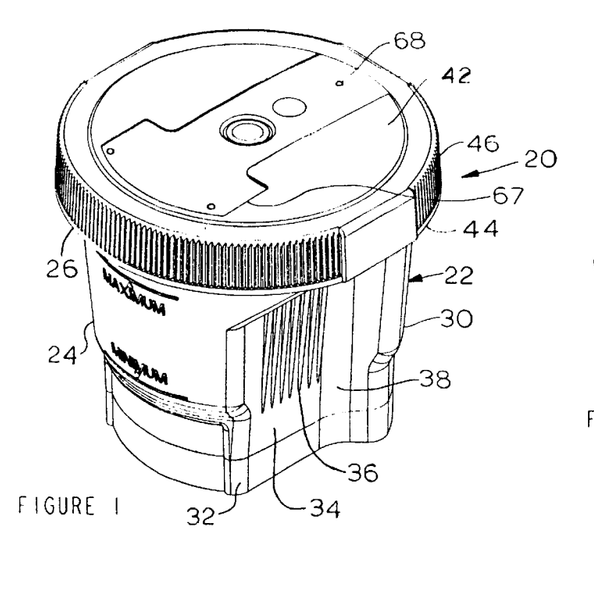
FIG. 1 is an isometric view showing the rear exterior of an assaying device in accordance with the present invention.
Figure 2:
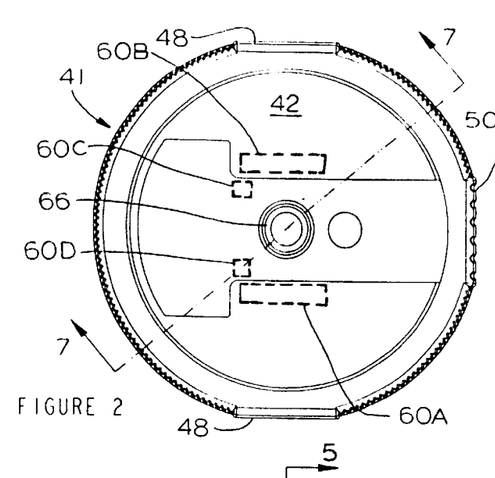
FIG. 2 is a top plan view of the assaying device of FIG. 1.
Figure 3:
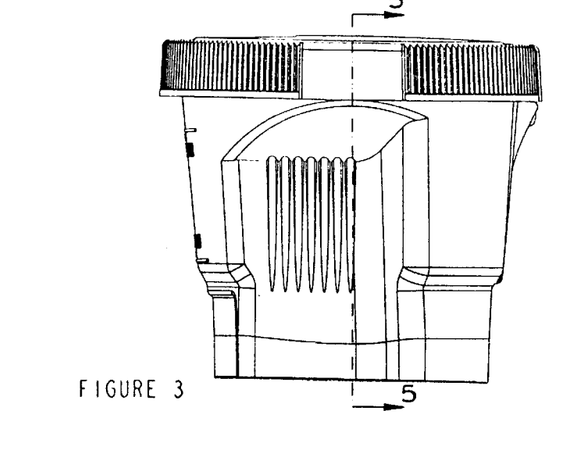
FIG. 3 is a left side view of the assaying device of FIG. 1.

Before proceeding with a discussion of the internal structure and operation. certain exterior characteristics of the housing 22 should be noted in FIGS. 1–3. Initially, note that the cup 24 has an irregular peripheral surface including an enlarged front portion 30 and a reduced rear portion 32. The reduced rear portion 32 is bounded by flat finger grip sides 34 having raised surface features 36 extending to an oblique wall surface 38. This irregular configuration of the cup facilitates easy manual handling of the cup enabling it to be readily grasped by the hand of a user and/or administrator.

The front enlarged portion 30 of the cup preferably includes (FIG. 9A) an area 39 characterized by multiple vertical fins 40. This area 39, as will be mentioned hereinafter, functions as a key or registration area to which an index area 50 on the cap must be aligned to assure proper cap/cup sealing.

Briefly, the cap 22 is comprised of a substantially circular member 41 having a top exterior surface 42 and a depending flange or skirt 44. The skirt 44 has a primarily knurled outer surface 46 that preferably defines flat areas 48 and an index area 50. The index area 50, which may be defined by vertical slots, is preferably used to align with the aforementioned cup area 39 to visually indicate to a user that the cap has been properly installed onto the cup. The cap 26 is preferably installed onto the cup via a mating thread 51. The cap 26 can carry a stop sooth 52 which rotates into engagement with the end fin 40 to assure proper installation of the cap onto the cup. When properly installed, the cap index area 50 will be aligned with the cup registration area 39. Alternative mounting mechanisms, e.g., bayonet mount, can be used to couple the cap 26 to the cup 24.

The cap top surface 42 is either transparent or at least defines one or more transparent areas, e.g., windows 60 (i.e., 60A, 60B, 60C, 60D) for enabling a test strip mounted beneath to be visible therethrough. As will be discussed hereinafter, the cap defines one or more compartments each of which accommodates a test strip which, when wetted by a fluid specimen, reacts to provide a visual indication indicative of a characteristic of the specimen.

Figure 4:
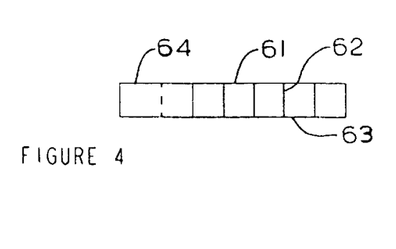
FIG. 4 is a diagrammatic view of a typical test strip used in embodiments of the present invention.

In the exemplary embodiment illustrated, the smaller windows 60C and 60D cover test strips intended to detect specimen (1) authenticity and (2) adulteration. As is well known, a freshly voided urine specimen can be authenticated by sensing various characteristics including its temperature and creatinine content. Adulteration of the specimen can be detected by known test strips sensitive to exogenous components. Larger windows 60A and 60B cover test strips intended to detect various specific chemical components typically associated with illegal substance abuse. FIG. 4 schematically represents such a test strip 61 showing multiple bands 62 visually represented on an indicator portion 63 extending from an absorbent portion 64. If the strip is being used to test for the presence of specific chemical components. the presence of such components will suppress the appearance of one or more of the visual bands 62. If all of the bands visually appear within a certain test interval , e.g., up to eight minutes, after the absorbent portion 64 has been wetted, this will indicate the absence of the specific chemical components sought. However, if any of those specific chemical components are present in concentrations above a certain threshold. their presence will suppress the appearance of one or more of the bands to indicate to an astute observer and/or computer based reader, the presence of such chemical components.

FIG. 2 also depicts a central opening 66 formed in the cap top surface 42. As will be discussed hereinafter, this opening 66 provides access to an aliquot delivery mechanism carried by the cap for delivering an aliquot of the fluid specimen in the cup to the test strips 61 carried beneath the windows 60. The top surface 42 also defines a "T" shaped area 67 intended to be used for a label preferably carrying bar code information for identification and tracking. Registration knobs 68 are formed in the area 67 to facilitate alignment of the label. The label preferably carries a self-adhesive on a portion of the label which can be adhered to the fins 40 on a cup 24 to create a tamper proof seal.

Figure 5A:
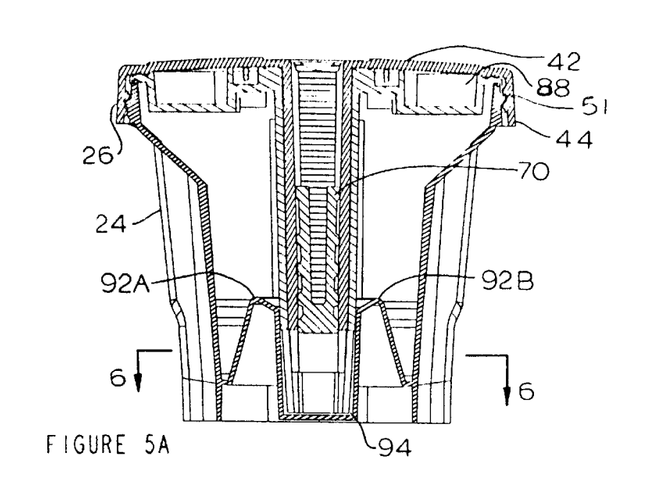
FIG. 5A is a sectional view taken substantially along the plane 5—5 of FIG. 3 showing the plunger in its actuated up position.
Figure 5B:
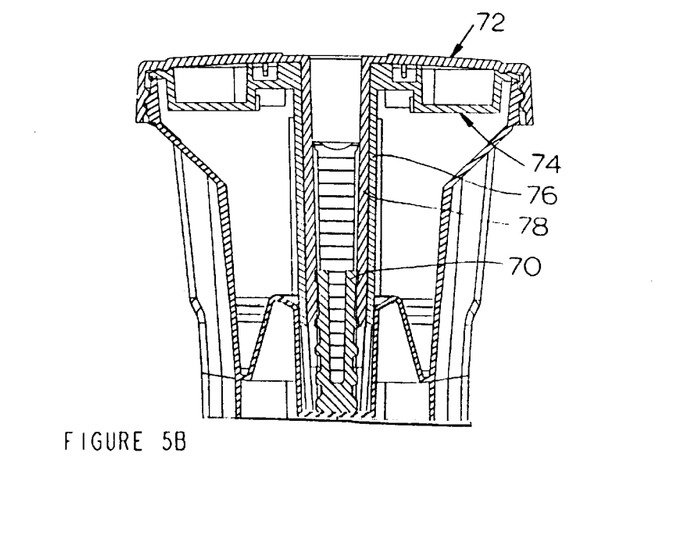
FIG. 5B is a sectional view similar to FIG. 5A but showing the plunger in its actuated down position.

Attention is now directed to FIGS. 5A and 5B which comprise vertical sectional views through the assaying device 20 showing its inner construction and operation. FIG. 5A illustrates a plunger 70 in its non-actuated up position whereas FIG. 5B illustrates the plunger 70 in its actuated down position.

Figure 7:
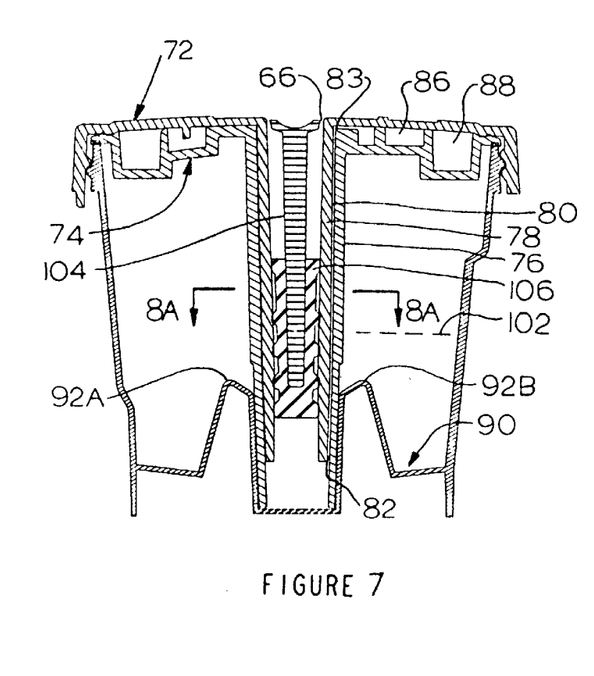
FIG. 7 is a sectional view taken substantially along the plane 7—7 of FIG. 2.
Figure 8A:
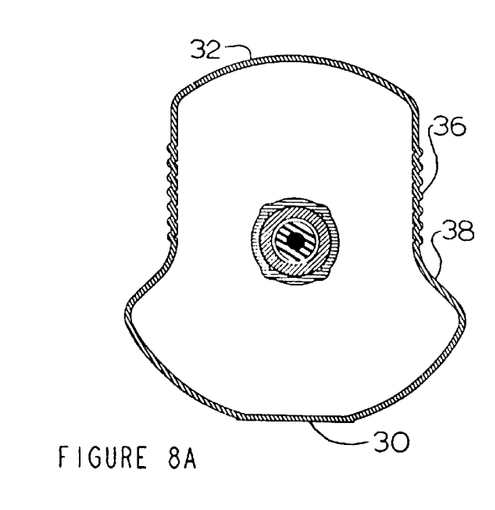
FIG. 8A is a sectional view taken substantially along the plane 8A—8A of FIG. 7.
Figure 8B:
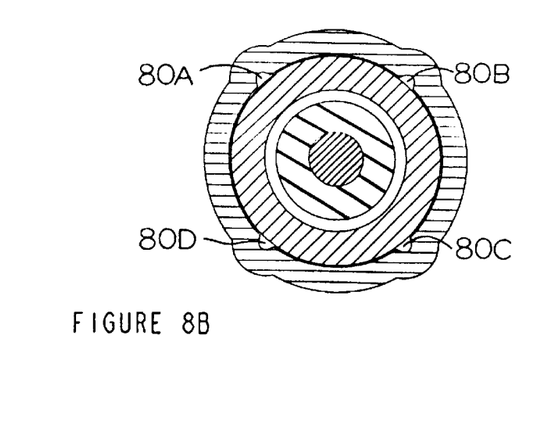
FIG. 8B is an enlarged sectional view of a portion of FIG. 8A.

As shown in FIGS. 5A and 5B, the cap 26 may be constructed of an upper cap member 72 and a lower cap member 74 which can be secured together as by welding or an appropriate adhesive. When assembled, the cap 26 defines descending concentric outer and inner tubular walls 76 and 78. As shown in FIGS. 7 and 8B, at least one passageway 80 extends vertically between the outer and inner tubular walls 76 and 78. As will be discussed in greater detail hereinafter, the passageway 80 defines a passageway inlet 82 at the lower end of inner tubular wall 78 and a passageway outlet 83 proximate to a test strip 61. Each test strip is accommodated in a compartment 86 formed in the cap between the cap upper member 72 and lower member 74. When the test strip absorbent portion 64 is wetted by fluid delivered by outlet 83, the strip will visually indicate one or more characteristics of the specimen as previously mentioned. A catch basin 88 is located adjacent to the compartment 86 to collect any fluid overflow from the absorbent portion.

Figure 6:
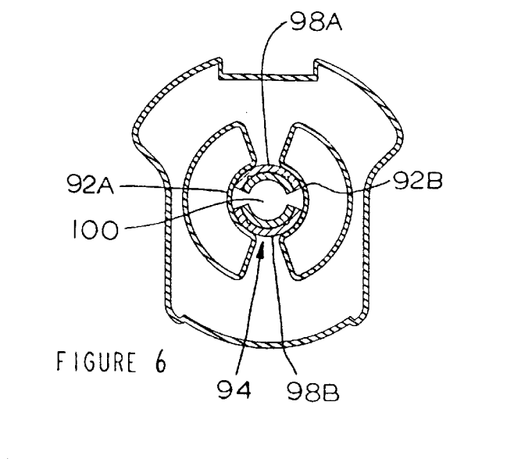
FIG. 6 is a sectional view taken substantially along the plane 6—6 of FIG. 5A showing the chamber for isolating a small specimen position.

As depicted in FIGS. 5–7, the inner floor 90 of the cup 24 is configured to define spaced first and second arcuate walls 92A, 92B, opposed to one another and defining an open well 94 therebetween. When the cap 26 is installed on the cup 24, as by aforementioned threads 51, the lower end of the outer tubular wall 76 extends into the well 94. The lower ends of the wall 76 essentially define partitions 98A. 98B which bridge the walls 92A, 92B to form a closed chamber 100 for isolating a portion of the fluid specimen. More particularly, initially assume that a fluid specimen has been collected in the open cup 24 to a level 102 (i.e., between the MAXIMUM and MINIMUM level lines depicted in FIG. 1) above walls 92A, 92B. When the cap 26 is then installed on the cup, a small portion of the specimen will be captured in the chamber 100 and isolated from the remainder of the specimen in the cup. The plunger 70, comprised of plunger pin 104 and plunger element 106. is mounted in inner tubular wall 78 above chamber 100. The plunger element 106, is formed of soft conforming material able to seal against the inner surface of inner tubular wall 78. The opening 66 in the cap upper surface 42 provides access to enable the pin 104 to be depressed either manually or by a machine operated piston.

As the plunger element 106 is depressed into chamber 100, the fluid therein is displaced upwardly via inlet 82 through passageway 80. Note that although passageway 80 has thus far been primarily referred to in the singular, the preferred embodiment depicted in the drawings, particularly FIG. 8B, shows the inclusion of multiple passageways 80, i.e., 80A, 80B, 80C, 80D. These passageways respectively extend to test strip compartments 86 (FIG. 11), i.e., 86A, 86B, 86C, 86D respectively located below the aforementioned cap windows 60A, 60B, 60C, and 60D. Thus, depression of the plunger 70 within the inner tubular wall 78 displaces fluid from the chamber 100 to deliver an aliquot to each of the compartments 86, each compartment accommodating a separate piece or strip of test material 61. The device 20 is constructed and dimensioned so that each aliquot comprises a specific volume of fluid, e.g., four drops.

Figure 9A:
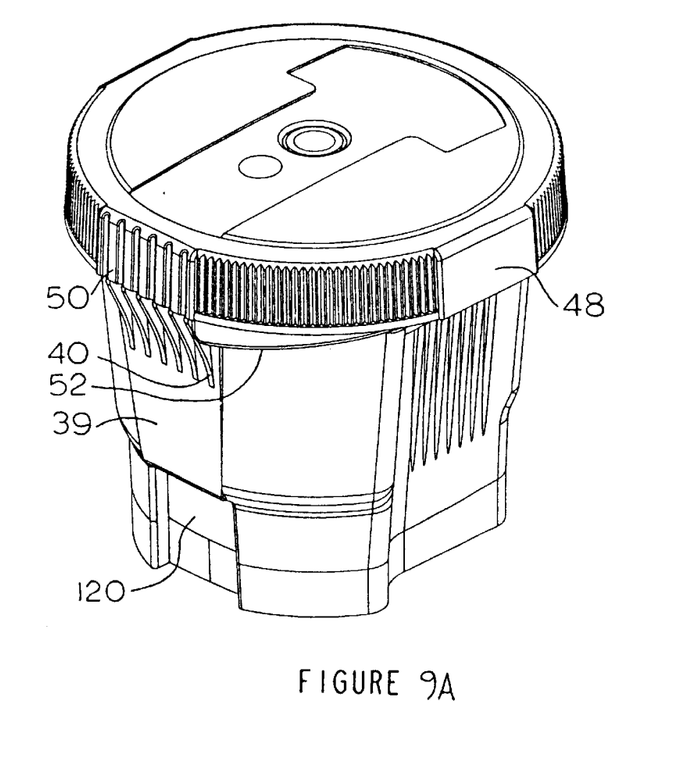
FIG. 9A is an isometric view of the assaying device of FIG. 1 showing the front exterior and FIG. 9B is a right side view of the assaying device.
Figure 9B:
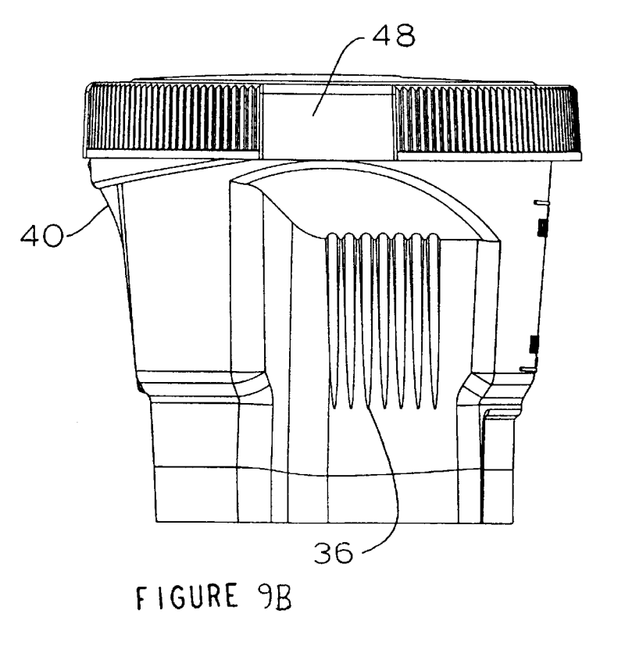

Attention is now specifically called to FIG. 9 which illustrates an isometric view of the front exterior of the assaying device 20. Note in FIG. 9 that the slotted portion 50 of the cap 26 is aligned with the finned portion 40 of the cup 22. This alignment indicates to a user that the cap is properly installed on the cup to seal the specimen therein. FIG. 9 also illustrates a recessed area 120 below the finned area 40. The recessed area 120 along with the flat areas 48 on the cap 26 are used to properly orient the assaying device cap relative to an automatic reader device, to be discussed hereinafter.

Figure 10:
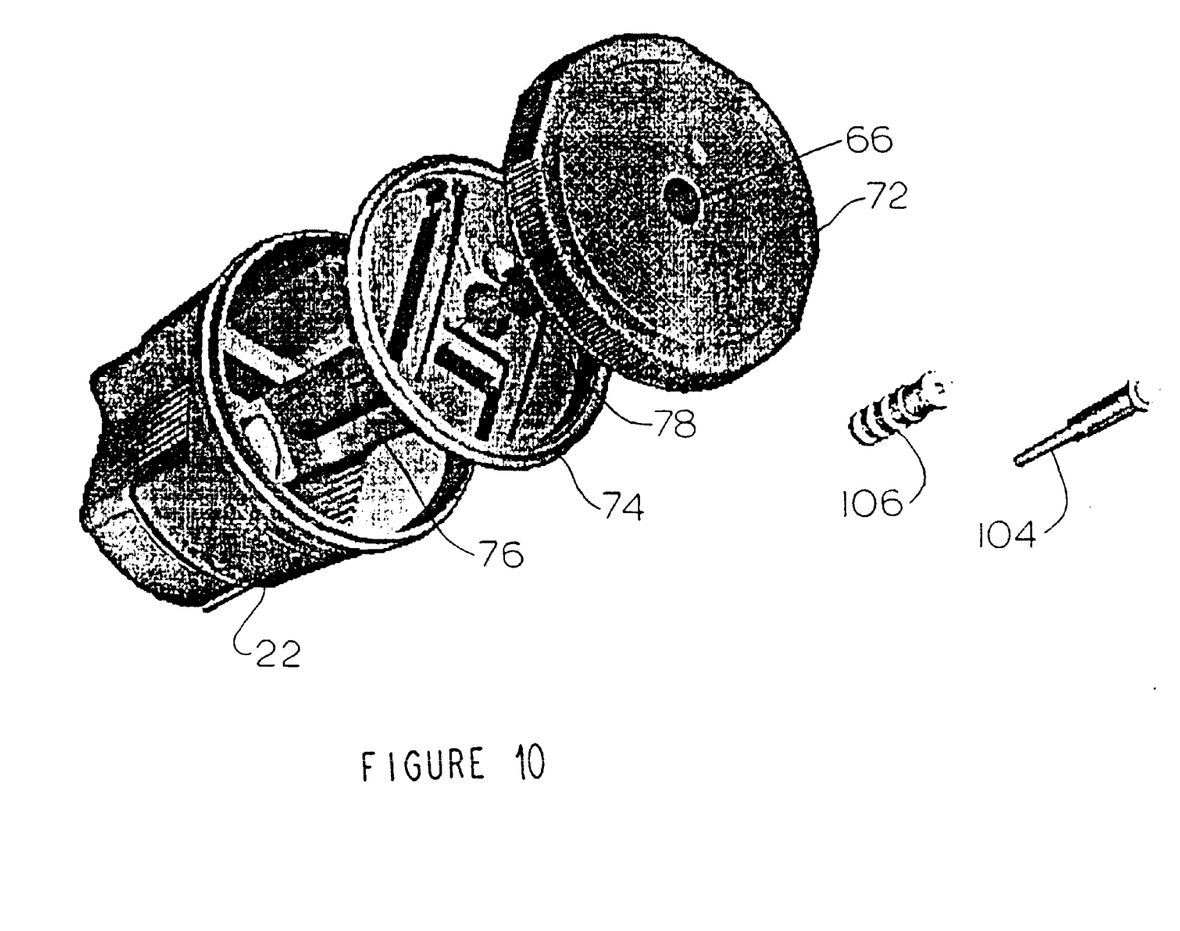
FIG. 10 is an exploded isometric view of the assaying device of FIG. 1.

Attention is now directed to FIG. 10 which illustrates an exploded isometric view of the assaying device 20 of FIGS. 1–9. More particularly, FIG. 10 shows the lower cap member 74 and upper cap member 72 spaced from one another and ready for insertion into the cup 24. The cap members 72, 74 are preferably joined together at the fabrication stage, e.g., by a suitable weld, prior to being made available for use. FIG. 10 also illustrates the plunger pin 104 and soft plunger element 106 ready for insertion through the opening 66 of cap top surface 42 into the interior of inner tubular wall 78. The tubular wall 78 then extends into the outer tubular wall 76 descending from the lower cap member 74.

Figure 11:
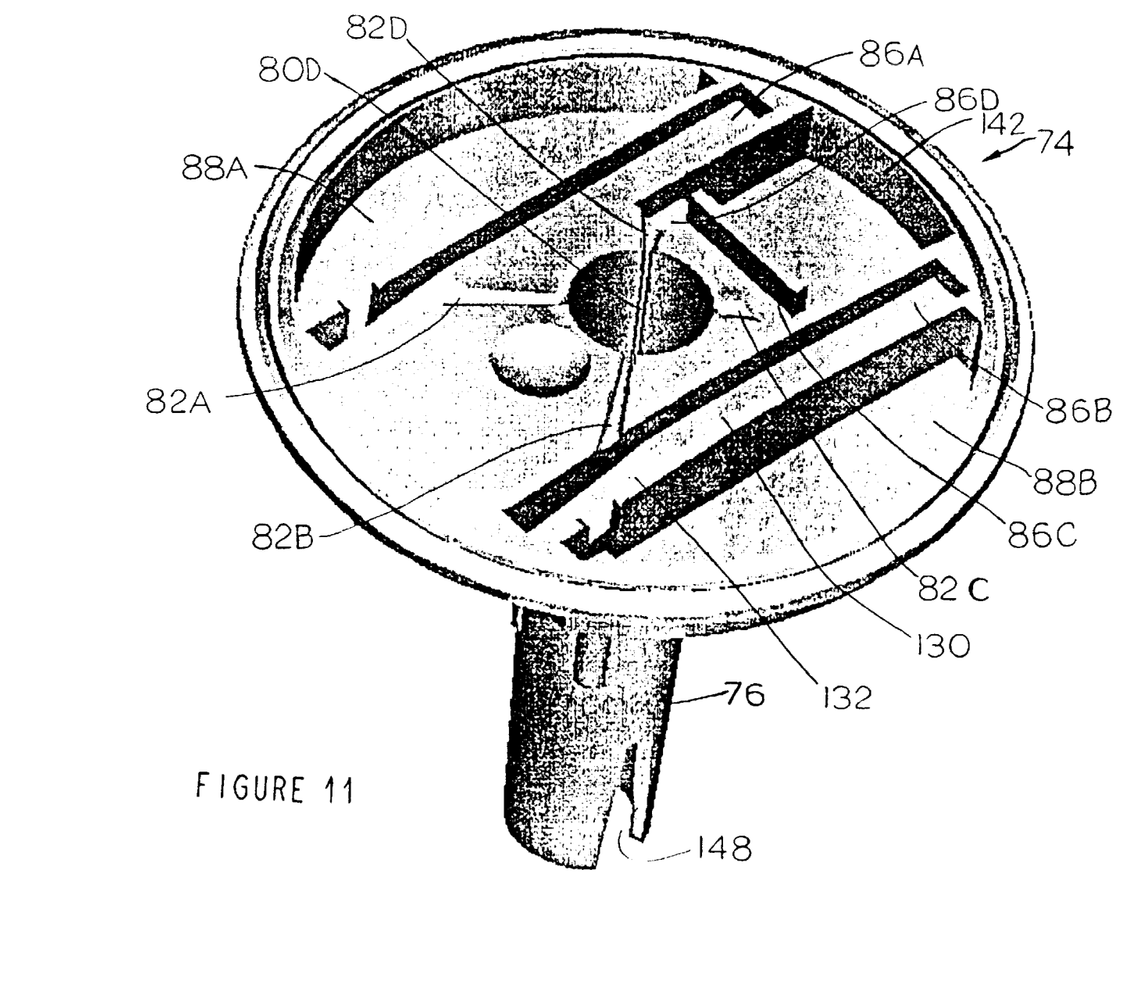
FIG. 11 is an enlarged isometric view of the lower cap member shown in FIG. 10.
Figure 12:
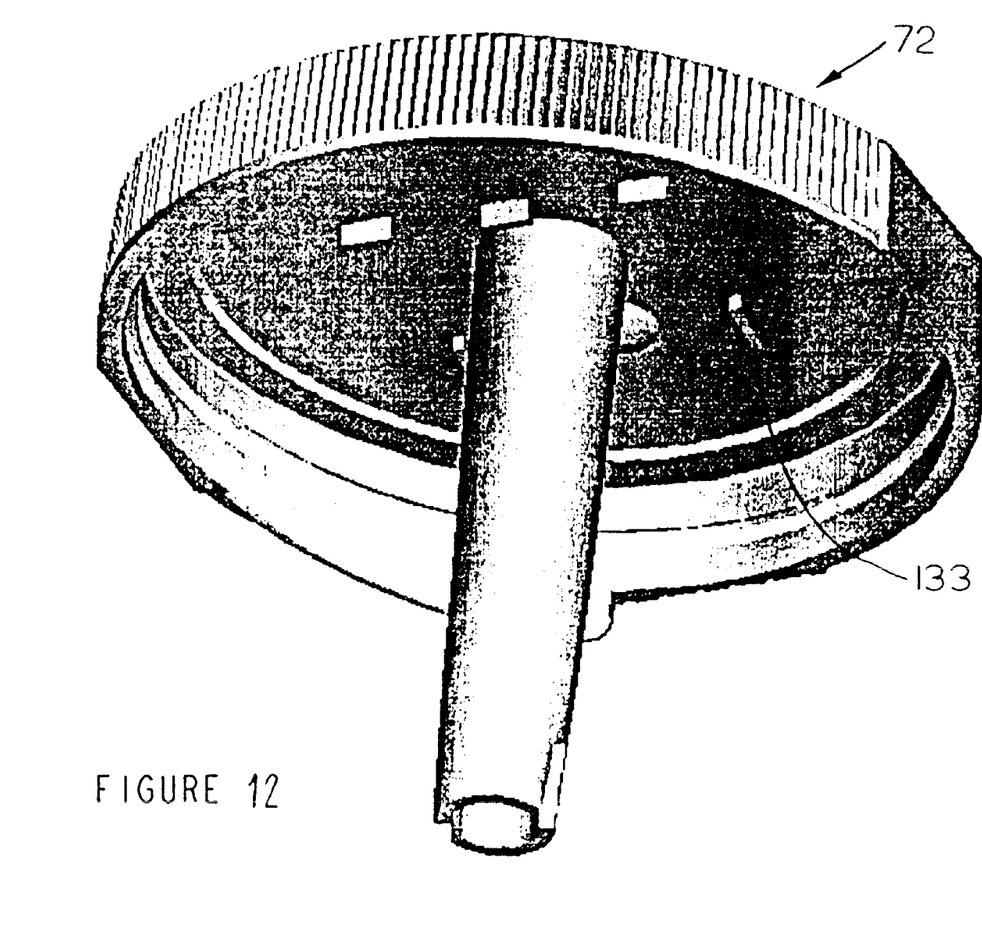
FIG. 12 is an enlarged isometric view of the upper cap member.

FIG. 11 shows in detail the geometry of the lower cap member 74 which together with the upper cap member 72 (FIG. 12) forms the aforementioned test strip compartments 86 and catch basins 88. Initially, note in FIG. 7 the passageways 80A, 80B, 80C, and 80D rising on the inner surface of outer tubular member 76. These vertical passageways join horizontally oriented passageway branches 82A, 82B, 82C, 82D shown in FIG. 11. Although not clearly visible in the drawings, the passageways preferably include simple unidirectional leaf valves to prevent backflow through the passageways. The lower cap member 74 defines compartments 86A, 86B each for accommodating a different test strip 61. Each compartment 86A, 86B is comprised of a flat bed area 130 and a sloped area 132. The test strip 61 is placed in the compartment 86 with the strip indicator portion 63 on area 130 and the strip absorbent portion 64 on area 132. Tabs 133 on the underside of upper cap member 72 press against and hold the test strips in the compartments 86. The vertical passageways 80A, 80B and passageway branches 82A, 82B respectively deliver an aliquot to the absorber portions of the test strips respectively in the compartments 86A, 86B. The sloped areas 132 formed immediately adjacent to compartment 86A and 86B carry excess fluid deposited onto the absorber portions into the catch basins 88A, 88B.

Note that the passageway branches 82C, 82D respectively lead to small compartments 86C, 86D intended to accommodate small test strips used primarily for authentication and adulteration checks, as previously described. For convenience in fabrication, compartments 86C, 86D can in fact be unified into a single physical compartment. Overflow from the compartments 86C, 86D flows into catch basin 142.

Figure 13:
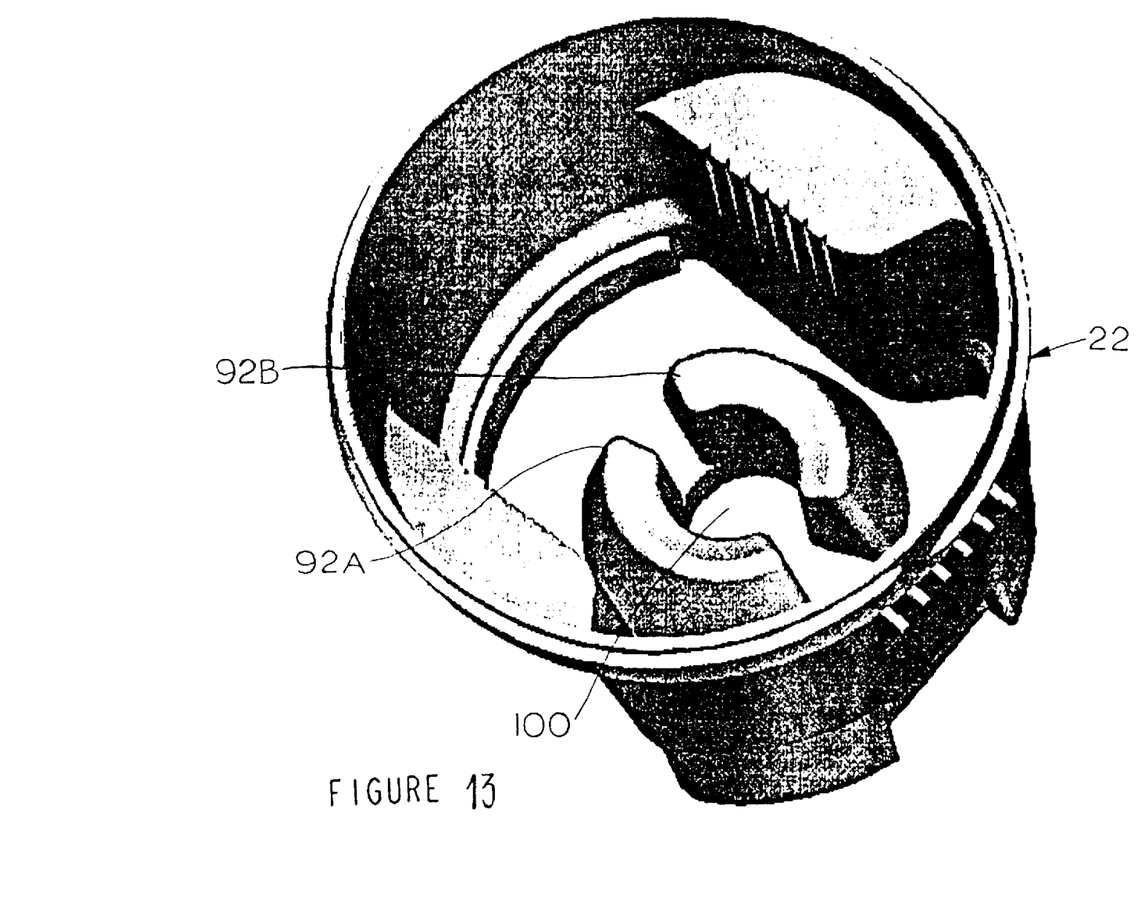
FIG. 13 is an isometric view primarily showing the cup interior.

Note in FIG. 11 the configuration of the lower end of outer tube 76. The tube includes opposed slots 148 in the tubular wall which form the aforementioned partitions 98A, 98B discussed in connection with FIG. 6. These partitions cooperate with the arcuate walls 92A, 92B shown in plan view in FIG. 6 and in isometric view in FIG. 13 to form chamber 100.

Figure 14:
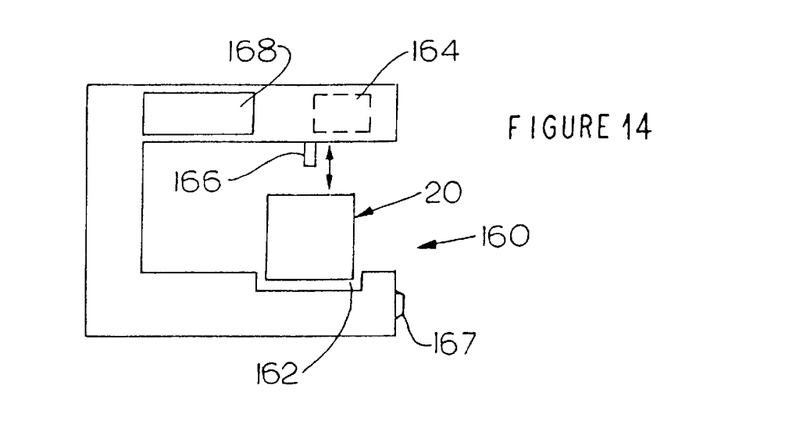
FIG. 14 is a schematic representation of a reader device useful in conjunction with the assaying device of FIGS. 1–13 for interpreting the visual indications produced by a test strip therein.

Attention is now directed to FIG. 14 which illustrates a reader device 160 for automatically reading the visual indications produced by the test strips in the assaying device 20 to generate data signals representative thereof. The reader device 160 defines a receptacle 162 for receiving the assaying device therein in a particular orientation. More particularly, the receptacle 162 is defined by surfaces intended to mate with key surfaces on the assaying device, e.g., cap flat areas 148 and/or recessed area 120, in order to compel the assaying device to a particular orientation. This orientation will place the aforementioned cap windows 60A. 60B, 60C, and 60D within the field of view of a camera 164 carried by the reader device.

The reader device 160 preferably also carries a reciprocally moveable piston 166 positioned in alignment with the opening 66 in an assaying device 20 properly oriented in the receptacle 162 for the purpose of actuating plunger 70. The reader device also preferably includes a START switch 167 and display panel 168.

Figure 15:
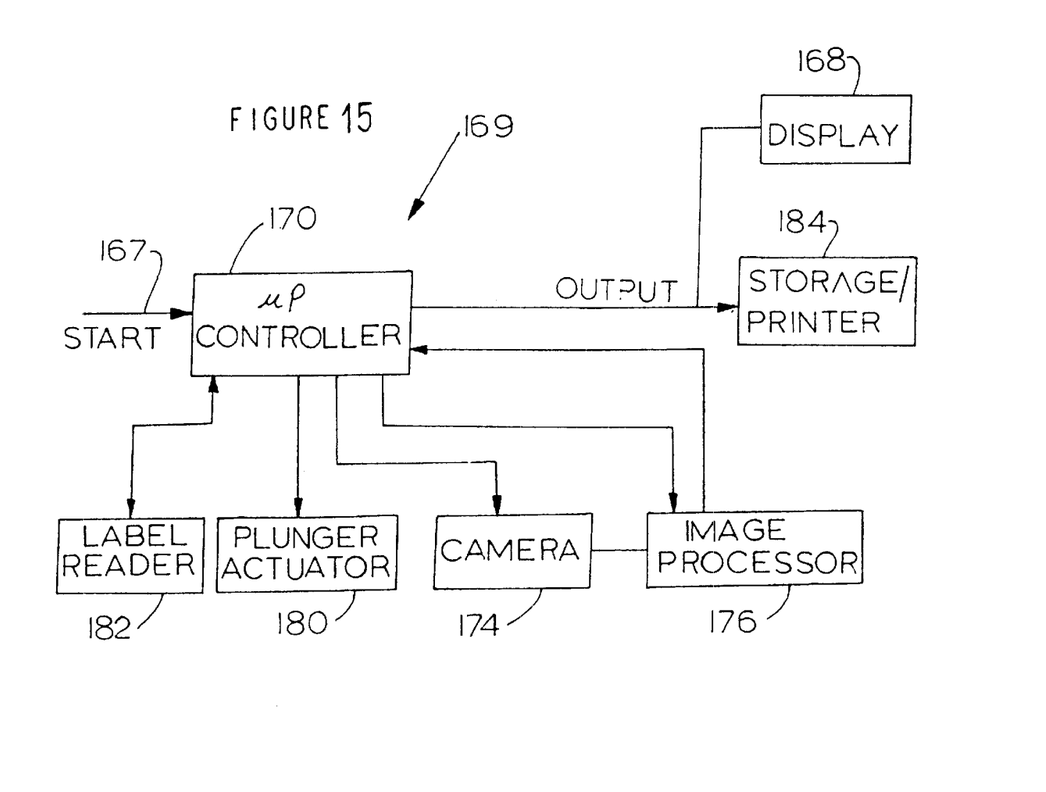
FIG. 15 is a functional block diagram depicting the microprocessor based controller of the reader unit of FIG. 14 for executing a test procedure in accordance with the present invention.

FIG. 15 depicts a functional block diagram of an electronic subsystem 169 utilized in the reader device 160. The subsystem 169 includes a microprocessor based controller 170, the camera 164, and an image processor 176. Although shown separately from the controller 170, the function of the image processor 176 could be performed by the microprocessor of controller 170.

The reader electronic subsystem 169 further includes a plunger actuator 180 which can, for example, comprise a solenoid for moving the piston 166 against the plunger 70. Additionally, the reader device can include a label reader module, e.g., a bar code reader 182, capable of reading a label adhered to the assaying device housing, for identification purposes. The electronic subsystem preferably further includes the aforementioned display panel 168 and an output module 184 for printing and/or storing data generated by the controller 170. The data may additionally be communicated, e.g., via modem (not show), to a remote site.

In the contemplated utilization of the assaying device 20, a staff person at a local site will give a user, e.g., an employee applicant, a new unused assaying device 20. The employee applicant will then deposit a fluid specimen into the cup to a level above the walls 92A, 92B. The cap 26 will then be installed onto the cup to a stop position which aligns the cap slotted area 50 with the finned area 39 of the cup 20. By so installing the cup 26 on the cup 24, the descending outer tubular wall 76 will capture and isolate a small portion of the fluid specimen in chamber 100.

The assaying device 20 will then be placed in the receptacle 162 of the reader unit 160 and switch 167 will be pressed to supply a start signal to microprocessor based controller 170. The controller 170 will then initiate and execute a test procedure which involves initially reading an identification label (not shown) carried by the cap assaying device 20. The controller 170 will then thrust the piston 166 into the cap opening 66 to drive the plunger 70 downwardly against the fluid specimen portion in chamber 100. This action will pump an aliquot from the isolated specimen portion via each of the passageways 80 to the test strips in the compartments 86A, 86B, 86C, 86D. Preferably. the controller will leave the piston 166 within the inner tubular wall 78 for the full duration of the test procedure to thus lock and prevent removal of the assaying device during the test procedure.

After an appropriate test interval, controller 170 will actuate camera 174 to cause it to generate an electronic representation of the visual indications provided by the respective test strips 61. The electronic representations generated by the camera 174 are then processed by the image processor 176 to interpret the characteristics of the fluid specimen. The resulting output data can then be displayed, stored, printed and/or communicated to a remote site, e.g. via modem. Unless this test produces a negative result, the entire assaying device 20 containing the uncontaminated specimen is then typically shipped to a remote laboratory for further analysis.

The foregoing describes applicants' preferred system for collecting and locally analyzing a fluid specimen. The preferred system includes an assaying device comprised of a fluid collection cup and a cap containing a mechanism actuatable to deliver an aliquot of the specimen to a test strip configured to produce a visually discernable reaction to the fluid. The visual reaction can be read by an imager, e.g., digital camera, and interpreted by a processor contained in a reader device to produce electronic data output suitable for data collection and reporting.

Although a preferred embodiment has been described, it is understood that many modifications and variations will occur to those skilled in the art which fall within the intended scope of the invention as defined by the appended claims.

What is claimed is:

1. A method for collecting a fluid specimen, locally analyzing an aliquot of said specimen, and preserving said specimen uncontaminated for further analysis, said method comprising:

collecting said specimen in an open cup;

providing a cup cap having a compartment for accommodating a test strip and a passageway providing an inlet to the interior of said cup and an outlet proximate to said compartment;

mounting said cap on said cup to seal said specimen therein and place said passageway inlet in contact with said specimen;

pumping an aliquot of said specimen from said passageway inlet to said passageway outlet to wet said test strip while preserving the specimen uncontaminated in said cup; and visually observing the reaction of said test strip.

2. The method of claim 1 wherein said pumping step includes the step of physically moving a plunger carried by said cap.

3. The method of claim 1 wherein said step of visually observing includes the steps of generating an electronic representation of an image of said test strip and processing said electronic representation to determine the presence of a specific chemical component.

* * * * *